(12) United States Patent
Wallace et al.

(10) Patent No.: US 7,368,616 B2
(45) Date of Patent: May 6, 2008

(54) METHOD FOR THE PRODUCTION OF MONOMERS USEFUL IN THE MANUFACTURE OF SEMICONDUCTIVE POLYMERS

(75) Inventors: Paul Wallace, Hertfordshire (GB); Carl Towns, Essex (GB); Thomas Pounds, Cambridge (GB)

(73) Assignee: Merck Patent GmbH (DE)

( * ) Notice: Subject to any disclaimer, the term of this patent is extended or adjusted under 35 U.S.C. 154(b) by 318 days.

(21) Appl. No.: 10/532,835

(22) PCT Filed: Oct. 29, 2003

(86) PCT No.: PCT/EP03/12022

§ 371 (c)(1),
(2), (4) Date: Apr. 26, 2005

(87) PCT Pub. No.: WO2004/039912

PCT Pub. Date: May 13, 2004

(65) Prior Publication Data
US 2005/0240011 A1    Oct. 27, 2005

(30) Foreign Application Priority Data
Oct. 30, 2002 (EP) ................................. 02024183

(51) Int. Cl.
*C07C 13/465* (2006.01)
(52) U.S. Cl. .............................. 585/27; 556/7; 528/394
(58) Field of Classification Search .................. 556/7; 528/394; 585/27
See application file for complete search history.

(56) References Cited

U.S. PATENT DOCUMENTS

| | | | |
|---|---|---|---|
| 5,523,555 A | 6/1996 | Friend et al. | |
| 5,621,131 A | 4/1997 | Kreuder et al. | |
| 5,723,873 A | 3/1998 | Yang | |
| 5,798,170 A | 8/1998 | Zhang et al. | |
| 6,268,695 B1 | 7/2001 | Affinito | |
| 6,329,534 B1 | 12/2001 | Kym et al. | |
| 6,423,519 B1 | 7/2002 | Bergnes et al. | |
| 6,653,438 B1 | 11/2003 | Spreitzer et al. | |
| 2001/0041802 A1 | 11/2001 | Kym et al. | |
| 2005/0038223 A1 | 2/2005 | Becker et al. | |

FOREIGN PATENT DOCUMENTS

| | | |
|---|---|---|
| DE | 198 46 767 | 4/2000 |
| EP | 0 430 033 | 6/1991 |
| EP | 0 707 020 | 4/1996 |
| EP | 0 842 208 | 5/1998 |
| EP | 0 851 714 | 7/1998 |
| EP | 0 880 303 | 11/1998 |
| EP | 0 901 176 | 3/1999 |
| EP | 0 947 123 | 10/1999 |
| EP | 0 949 850 | 10/1999 |
| EP | 1 078 917 | 2/2001 |
| GB | 2 348 316 | 9/2000 |
| WO | WO-90/13148 | 11/1990 |
| WO | WO-95/25086 | 9/1995 |
| WO | WO-96/16449 | 5/1996 |
| WO | WO-97/33323 | 9/1997 |
| WO | WO-98/10621 | 3/1998 |
| WO | WO-99/54385 | 10/1999 |
| WO | WO-00/00374 | 1/2000 |
| WO | WO-00/03743 | 1/2000 |
| WO | WO-00/22026 | 4/2000 |
| WO | WO-00/46321 | 8/2000 |
| WO | WO-00/48258 | 8/2000 |
| WO | WO-00/53656 | 9/2000 |
| WO | WO-00/55927 | 9/2000 |
| WO | WO-01/19142 | 3/2001 |
| WO | WO-01/81649 | 11/2001 |
| WO | WO-02/26859 | 4/2002 |
| WO | WO-03/020790 | 3/2003 |

OTHER PUBLICATIONS

Nahm et al., "N-Methoxy-N-Methylamides as Effective Acylating Agents", *Tetrahedron Letters*, vol. 22, pp. 3815-3818 (1981).
Wallace et al., "Observations on the DDQ Oxidation of 1-Acyldihydropyridines—A Synthetic Application", *Synthesis*, No. 12, pp. 1784-1789 (2001).
Colletti et al., "Hybrid-Designed Inhibitors of p38 MAP Kinase Utilizing *N*-Arylpyridazinones", *J. Med. Chem.*, vol. 46, pp. 349-352 (2003).

*Primary Examiner*—Rei-tsang Shiao
(74) *Attorney, Agent, or Firm*—Connolly Bove Lodge & Hutz LLP

(57) ABSTRACT

The instant invention relates to a new method for the synthesis of monomers and their use inter alia in the manufacture of semiconductive polymers. Monomers, in particular, asymmetric monomers, such as asymmetric fluorene compounds, are valuable material in the manufacture of semiconductive polymers. The know methods for producing asymmetric monomers, such as asymmetric fluorene compounds, are expensive due to the formation of by-products.

The method according to the present invention avoids the formation of such by-products and is described in more detail in claims 1 to 14.

16 Claims, No Drawings

METHOD FOR THE PRODUCTION OF MONOMERS USEFUL IN THE MANUFACTURE OF SEMICONDUCTIVE POLYMERS

RELATED APPLICATIONS

This application is a national stage application (under 35 U.S.C. 371) of PCT/2003/012022 filed Oct. 29, 2003 which claims benefit to European Patent Application 02024183.2 filed Oct. 30, 2002.

FIELD OF THE INVENTION

This invention relates to a new method for the synthesis of monomers and their use inter alia in the manufacture of semiconductive polymers.

BACKGROUND OF THE INVENTION

Electroactive polymers are now frequently used in a number of optical devices such as in polymeric light emitting diodes ("PLEDs") as disclosed in WO 90/13148, photovoltaic devices as disclosed in WO 96/16449 and photodetectors as disclosed in U.S. Pat. No. 5,523,555. One class of electroluminescent polymers are polyfluorenes as disclosed in, for example, Adv. Mater. 2000 12(23) 1737-1750. These polyfluorenes have the advantages of being soluble in conventional organic solvents and have good film forming properties. Furthermore, fluorene monomers are amenable to Suzuki or Yamamoto polymerisation which enables a high degree of control over the regioregularity of the resultant polymer and the formation of block copolymers wherein different blocks have different functions as disclosed in WO 00/55927.

Each fluorene repeat unit of these polyfluorenes is normally provided with two 9-substituents to modify the properties of the polymer. For example, alkyl groups have been used as 9-substituents for the purpose of increasing the solubility of the polymer. Other substituents, such as phenyl, have also been used.

The two 9-substituents are often the same for simplicity of manufacture, however this means that the fluorene repeat unit is symmetric which has been found to be problematic in that polymers comprising symmetrical fluorene repeat units have a tendency to aggregate.

To overcome this problem, efforts have been directed towards production of asymmetric fluorene monomers, i.e. fluorene monomers wherein the two 9-substituents are different, as disclosed in WO 00/22026 and DE 19846767. Processes disclosed in these documents include reaction of fluorenone or biphenyl-2-carboxylic acid ester with two different organometallics.

Biphenyl-2-amides are known—see for example WO 00/03743 and U.S. Pat. No. 6,329,534. However, these disclosures do not teach such carboxamides comprising polymerisable groups, asymmetric substitution or a method of forming monomers therefrom. Tetrahedron Letters 22(39), 3815-3818, 1981, describes a process of reacting N-methoxy amides with organometallic reagents to form ketones. The reaction proceeds via a 5-membered intermediate that is resistant to over-reaction to form an alcohol. This disclosure is not concerned with the formation of asymmetric systems, polycyclic systems or monomers.

SUMMARY OF THE INVENTION

The present inventors have found that the prior art methods of forming asymmetric compounds, in particular asymmetric fluorene compounds, have drawbacks. When an ester starting material is used, the inventors have found that some of the starting material may not react at all with the first organometallic, and the proportion that does react may go on to react with a second equivalent resulting in a symmetric fluorene. Additional by-products may also form. Thus, the desired ketone intermediate is not only present in low quantities, it is also difficult to separate from the other products and residual starting material.

It is therefore a purpose of the present invention to provide a material for production of an asymmetric monomer that is not susceptible to over-reaction to form a symmetric monomer and that does not present difficulties in isolating the desired product. It is a further purpose of the invention to provide a method of forming a monomer via use of said material.

The present inventors have devised a method of forming polycyclic compounds with asymmetric substituents, in particular compounds suitable for use as monomers, via an amide starting material. In addition to the reaction of the amide, the method of the present invention includes the further steps of reacting the resultant ketone with a further equivalent of a different organometallic reagent and the yet further step of a ring closing elimination reaction.

Accordingly, in a first aspect the invention provides a method according to scheme 1 of forming a compound of formula (IV):

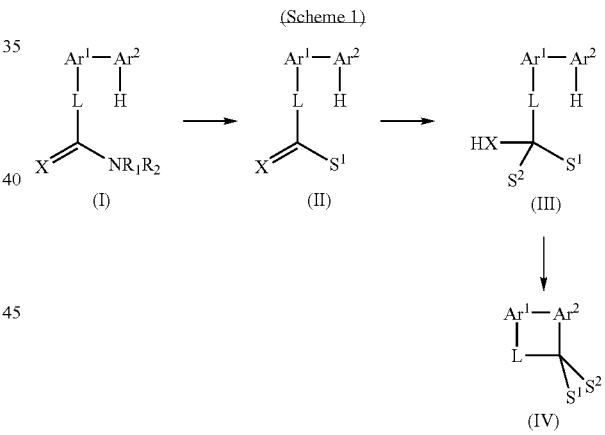

said method comprising the steps of:
a) reacting a compound of formula (I) with a compound of formula $S^1$-M to give a compound of formula (II);
b) reacting the compound of formula (II) with a compound of formula $S^2$-M to give a compound of formula (III); and
c) eliminating $H_2X$ from the compound of formula (III) to give a compound of formula (IV).

wherein
$Ar^1$ and $Ar^2$ are independently selected from optionally substituted aryl or heteroaryl groups;
X is selected from O, S, NH and NR;
L is a bond or a linking group of 1, 2 or 3 atoms,
R and $R^1$ are independently selected from optionally substituted alkyl, alkylaryl, arylalkyl, aryl and heteroaryl groups;

$R^2$ is selected from the group consisting of alkoxy, aryloxy, arylalkyloxy, alkylaryloxy, alkylthio, arylthio, alkylarylthio, arylalkylthio;

H is bound to a carbon atom C' of $Ar^2$;

C' and the carbon atom of C=X are separated by 3-5 atoms;

$S^1$ and $S^2$ are each selected from optionally substituted alkyl, aryl or heteroaryl groups;

M comprises a metal; and

M is linked to $S^1$ and $S^2$ by a carbon-metal bond.

Preferably, alkyl is $C_1$-$C_{20}$-alkyl which can be each straight-chain, branched or cyclic, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, in particular preferred methyl, ethyl, n-propyl, i-propyl, n-butyl, i-butyl, s-butyl, t-butyl, n-pentyl, s-pentyl, cyclopentyl, n-hexyl, cyclohexyl, n-octyl or cyclooctyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, arylalkyl is $C_7$-$C_{20}$-arylalkyl, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, in particular preferred o-tolyl, m-tolyl, p-tolyl, 2,6-dimethylphenyl, 2,6-diethylphenyl, 2,6-di-i-propylphenyl, 2,6-di-t-butylphenyl, o-t-butylphenyl, m-t-butylphenyl or p-t-butylphenyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryl is $C_7$-$C_{20}$-alkylaryl, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, in particular preferred benzyl, ethylphenyl, propylphenyl, diphenylmethyl, triphenylmethyl or naphthalinylmethyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryl is $C_6$-$C_{20}$-aryl, in particular preferred phenyl, biphenyl, naphthyl, anthracenyl, triphenylenyl, [1,1';3',1"]terphenyl-2'-yl, binaphthyl or phenanthreny.l Preferably, heteroaryl is $C_5$-$C_{20}$-heteroaryl, in particular preferred 2-pyridyl, 3-pyridyl, 4-pyridyl, chinolinyl, isochinolinyl, acridinyl, benzochinolinyl or benzoisochinolinyl. Preferably, alkoxy is $C_1$-$C_{20}$-alkoxy, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, in particular preferred methoxy, ethoxy, n-propoxy, i-propoxy, n-butoxy, i-butoxy, s-butoxy or t-butoxy, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryloxy is $C_6$-$C_{20}$-Aryloxy, in particular preferred phenoxy, naphthoxy, biphenyloxy, anthracenyloxy or phenanthrenyloxy.

Preferably, arylalkyloxy is $C_7$-$C_{20}$-arylalkyloxy where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryloxy is $C_7$-$C_{20}$-alkylaryloxy, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylthio is $C_1$-$C_{20}$-alkylthio where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$— and $R^{10}$, $R^{11}$, $R^{12}$, $R^{13}$ are identical or different and are hydrogen or an aliphatic or aromatic hydrocarbon radical having 1 to 20 carbon atoms.

Preferably, arylthio is $C_6$-$C_{20}$-arylthio.

Preferably, alkylarylthio is $C_7$-$C_{20}$-alkylarylthio where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, arylalkylthio is $C_7$-$C_{20}$-arylalkylthio, where one or more non-adjacent CH2 groups may be replaced by oxygen, sulphur, —CO—, —COO—, —O—CO—, $NR^{10}$—, —$(NR^{11}R^{12})^{+}$-$A^{-}$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Intermediate products (II) and (III) may or may not be isolated from the reaction mixture prior to the subsequent step according to the method of the first aspect of the invention.

Each aryl group $Ar^1$ and $Ar^2$ may comprise a monocyclic or fused ring system.

Preferably, $Ar^1$ and $Ar^2$ are each phenyl or substituted phenyl.

Preferably, X is O or S.

Preferably, L is a bond.

Preferably, R is C1-10 alkyl

Preferably, $R^1$ is C1-10 alkyl.

Preferably, $R^2$ is C1-10 alkoxy.

Preferably, M is lithium, zinc or Mg-Hal wherein Hal is a halide.

Preferably, $S^1$ and $S^2$ are independently selected from optionally substituted aryl or alkyl, in particular preferred $S^1$ and $S^2$ are different from each other.

In one preferred embodiment of the first aspect of the invention, $Ar^1$ and $Ar^2$ of the compound of formula (I) are each substituted with a polymerisable group P.

In a second preferred embodiment of the first aspect of the invention, there is a further step of providing each of $Ar^1$ and $Ar^2$ of the compound of formula (II), (III) or (IV) with a polymerisable group P.

Preferably, each polymerisable group P is independently a leaving group capable of participating in a polycondensation reaction, more preferably a metal insertion reaction with a nickel or palladium complex catalyst. Most preferably, each P is independently selected from a halide, (preferably chlorine, bromine or iodine, most preferably bromine; a boron derivative group selected from a boronic acid group, a boronic ester group and a borane group; or a moiety of formula —O—$SO_2$-Z wherein Z is selected from the group consisting of optionally substituted alkyl and aryl.

The method of the first aspect of the invention preferably comprises the step of polymerising the compound of formula (IV) by reaction of polymerisable group P.

According to one preferred method of polymerisation, each polymerisable group P is a halide and the compound of formula (IV) is polymerised in a reaction mixture comprising a catalytic amount of a nickel (0) catalyst suitable for catalysing the polymerisation of the compound of formula (IV).

According to another preferred method of polymerisation, at least 1 polymerisable group P is a boron derivative group and the compound of formula (IV) is polymerised in a reaction mixture comprising a catalytic amount of a palladium catalyst suitable for catalysing the polymerisation of the compound of formula (IV), and a base sufficient to convert the boron derivative functional groups into boronate anionic groups.

The compound of formula (IV) may or may not be isolated from the reaction mixture in which it is formed prior to its polymerisation.

In a second aspect, the invention provides a method for the production of an optical device or a component for an optical device, which comprises providing a substrate, producing a polymer in accordance with the first aspect of the invention and depositing the polymer on the substrate. Preferably, the optical device comprises an electroluminescent device.

In a third aspect, the invention provides an optionally substituted compound of formula (V):

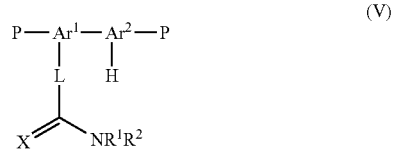

(V)

wherein $Ar^1$, $Ar^2$, L, X, $R^1$ and $R^2$ are as defined in formula (I) of Scheme 1; P is independently selected from a halide, preferably chlorine, bromine or iodine, most preferably bromine, or a boron derivative group selected from a boronic acid group, a boronic ester group and a borane group, H is bound to a carbon atom C' of $Ar^2$; and C' and the carbon atom of C=X are separated by 3-5 atoms.

Preferably, each $Ar^1$ and $Ar^2$ is phenyl or substituted phenyl.

Preferably, X is O, S.

Preferably, L is a bond.

Preferably, each P is independently selected from a halide or a boron derivative group selected from a boronic acid group, a boronic ester group and a borane group.

Preferably, $R^1$ is C1-10 alkyl.

Preferably, $R^2$ is C1-10 alkoxy.

Preferably, the compound of the third aspect of the invention is a compound of formula (VI):

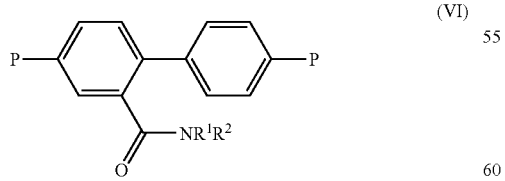

(VI)

wherein P, $R^1$ and $R^2$ are as defined in formula (V) above.

The present inventors have surprisingly found that compounds of formula (IV) may be prepared according to the method of the invention without over-reaction to form symmetric compounds and with the product being obtained in high purity. In particular, compounds of formula (IV) may be prepared using compounds of formula (VI).

Furthermore, the present inventors have surprisingly found that the method of the present invention is effective with standard organometallic reagents (such as organolithium or Grignard reagents) whereas the prior art methods may only be effective with the more reactive reagents such as organolithium. Finally, the present inventors have found that a wider range of substituents $S^1$ and/or $S^2$ may be provided by the method of the invention than by the aforementioned prior art methods. As a result, a straightforward route to a wider range of asymmetric monomers is made available which in turn provides greater flexibility in terms of synthesis of polymers and copolymers with improved solubility, morphology, etc.

DETAILED DESCRIPTION OF THE INVENTION

The method of the invention may be employed to prepare symmetric or asymmetric compounds, in particular symmetric or asymmetric fluorenes, wherein both substituents are aromatic, in particular phenyl; both substituents are aliphatic, in particular C1-10 branched or linear alkyl; or one substituent is aromatic and the other substituent is aliphatic. Accordingly, a wide range of materials with differing substituents, and therefore different electronic properties, may be prepared.

Examples of asymmetric compounds that may be formed according to this method include asymmetric fluorenes and asymmetric indenofluorenes as illustrated below:

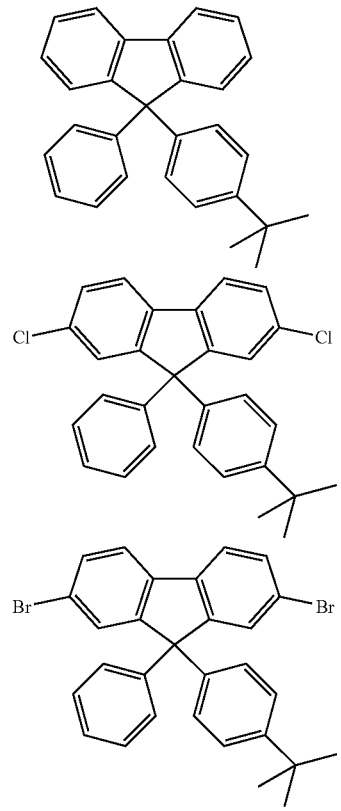

-continued
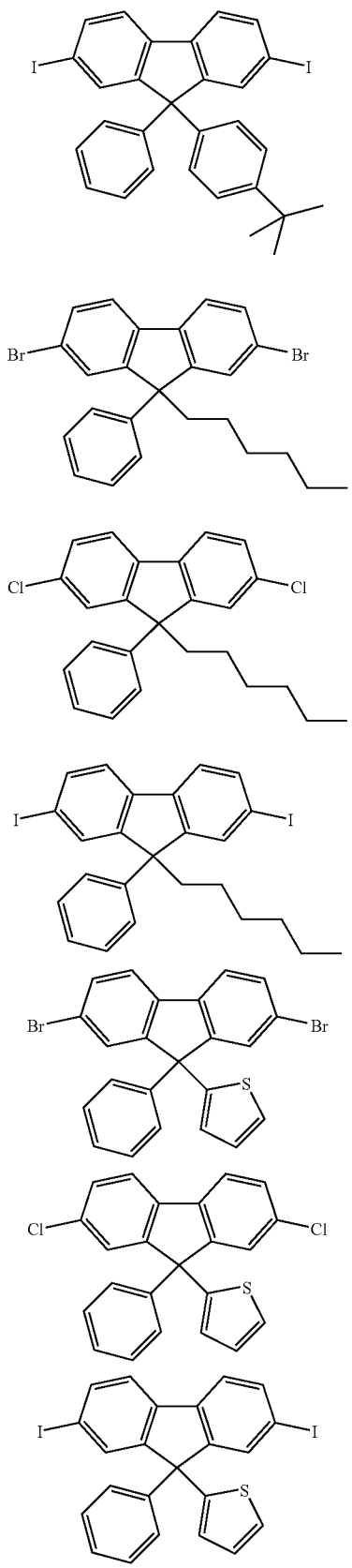
-continued
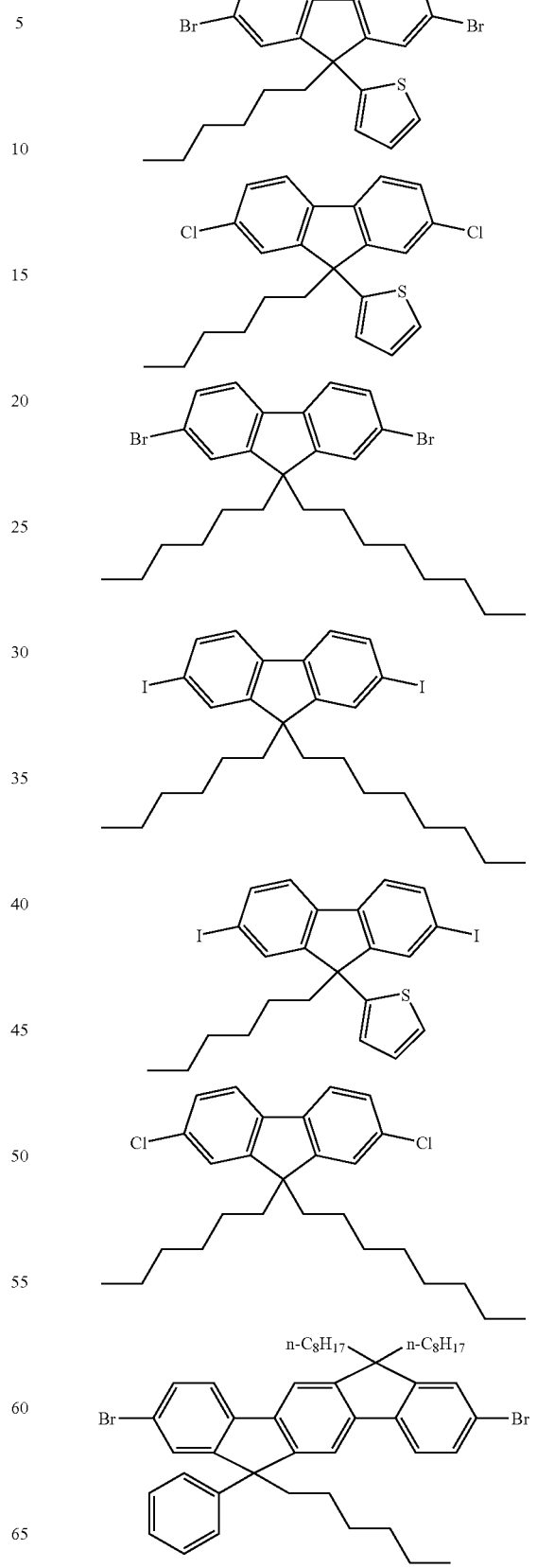

-continued

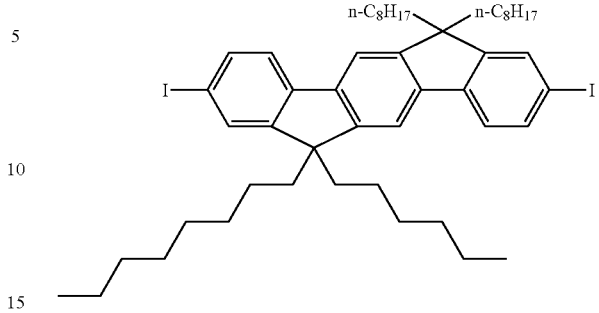

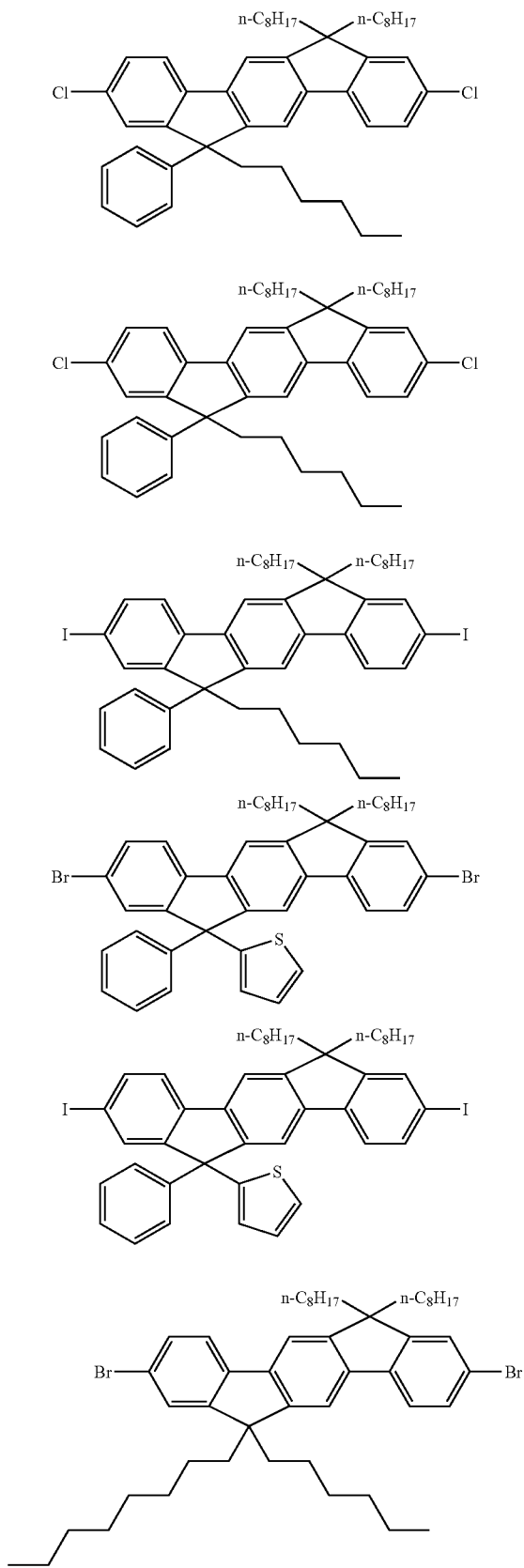

The materials prepared in accordance with the invention may be useful as monomers, in particular monomers for the preparation of electroactive, more particularly semiconducting, polymers. These polymers may be homopolymers or copolymers.

The monomers according to the invention preferably comprise only two reactive groups P in order that linear polymers be produced, however monomers with more than two P groups, e.g. for production of cross-linked polymers, are also within the scope of the invention.

The asymmetric monomers according to the invention may be formed from a range of combinations of groups $S^1$ and $S^2$ including, but not limited to the following:

$S^1$=unsubstituted phenyl; $S^2$=phenyl bearing one or more alkyl or alkoxy substituents;

$S^1$ and $S^2$ are both phenyl, each bearing a different alkyl or alkoxy substituent and/or the same alkyl or alkoxy groups substituted in different positions;

$S^1$=optionally substituted phenyl or heteroaryl; $S^2$=optionally substituted alkyl;

$S^1$=optionally substituted phenyl; $S^2$=optionally substituted heteroaryl.

The compound of formula (IV) according to the invention is preferably a fluorene bearing substituents $S^1$ and $S^2$.

The polymers prepared using monomers according to the invention may be homopolymers or copolymers. A wide range of co-monomers for polymerisation with the monomers of the invention will be apparent to the skilled person. Examples of comonomers include triarylamines as disclosed in, for example, WO 99/54385 and heteroaryl units as disclosed in, for example, WO 00/46321 and WO 00/55927.

Where the polymer according to the invention is a copolymer, it may possess the repeat unit of the invention with one or more different co-repeat units. One class of co-repeat units is arylene repeat units, in particular: 1,4-phenylene repeat units as disclosed in J. Appl. Phys. 1996, 79, 934; fluorene repeat units as disclosed in EP 0842208, trans-indenofluorene repeat units as disclosed in, for example, Macromolecules 2000, 33(6), 2016-2020; spirobifluorene repeat units as disclosed in, for example EP 0707020; and stilbene repeat units (commonly known as "OPV" repeat units) as disclosed in WO 03/020790. Each of these repeat units is optionally substituted. Examples of substituents include solubilising groups such as $C_{1-20}$alkyl or alkoxy; electron withdrawing groups such as fluorine, nitro or cyano; and substituents for increasing glass transition temperature (Tg) of the polymer such as bulky groups, e.g. tert-butyl or optionally substituted aryl groups.

Particularly preferred triarylamine repeat units for such copolymers include units of formulae 1-6:

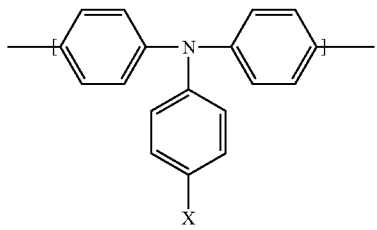

1

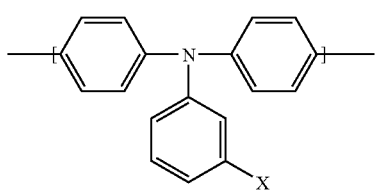

2

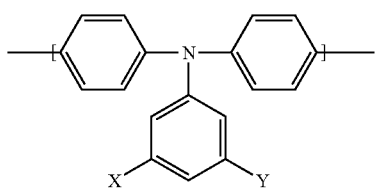

3

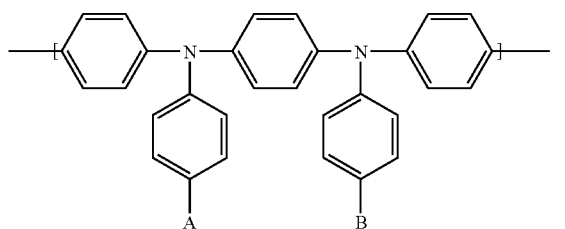

4

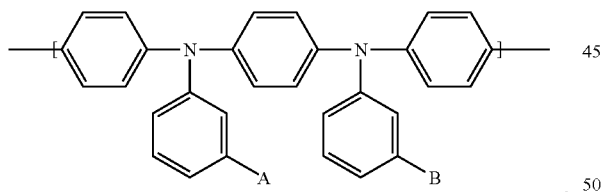

5

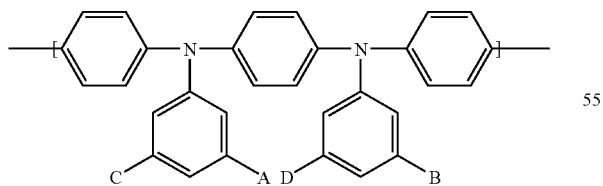

6

X and Y may be the same or different and are substituent groups. A, B, C and D may be the same or different and are substituent groups. It is preferred that one or more of X, Y, A, B, C and D is independently selected from the group consisting of alkyl, aryl, perfluoroalkyl, thioalkyl, cyano, alkoxy, heteroaryl, alkylaryl and arylalkyl groups. One or more of X, Y, A, B, C and D also may be hydrogen. It is preferred that one or more of X, Y, A, B, C and D is independently an unsubstituted, isobutyl group, an n-alkyl, an n-alkoxy or a trifluoromethyl group because they are suitable for helping to select the HOMO level and/or for improving solubility of the polymer.

Particularly preferred heteroaryl repeat units for such copolymers include units of formulae 7-24:

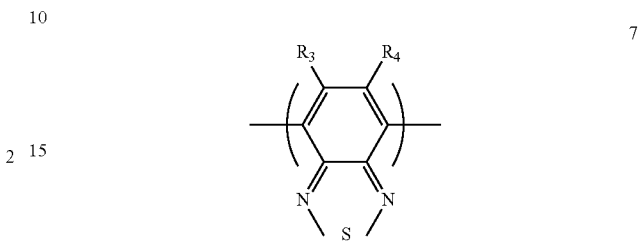

7 wherein $R_3$ and $R_4$ are the same or different and are each independently a substituent group. Preferably, one or more of $R_1$, $R_2$, $R_3$ or $R_4$ may be selected from hydrogen, alkyl, aryl, perfluoroalkyl, thioalkyl, cyano, alkoxy, heteroaryl, alkylaryl, or arylalkyl. These groups are preferred for the same reasons as discussed in relation to X, Y, A, B, C and D above. Preferably, for practical reasons, $R_3$ and $R_4$ are the same. More preferably, they are the same and are each a phenyl group.

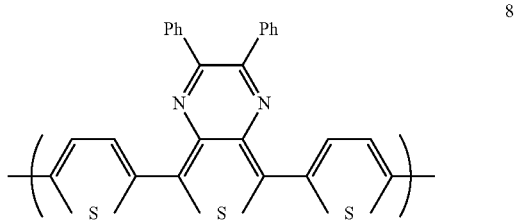

8

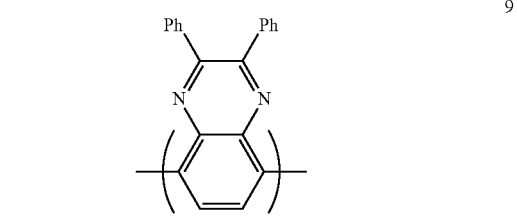

9

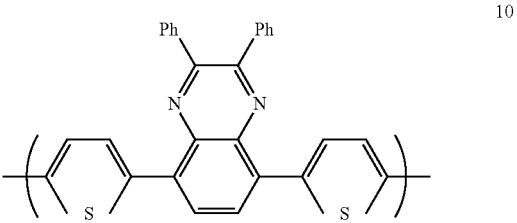

10

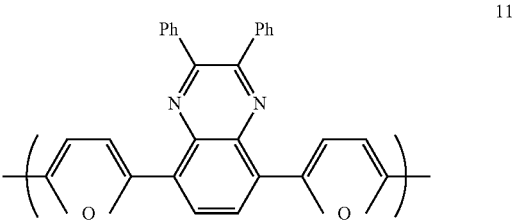

11

-continued

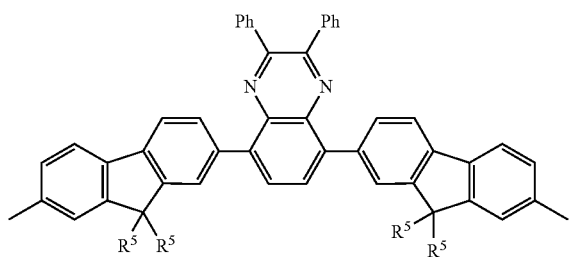
12

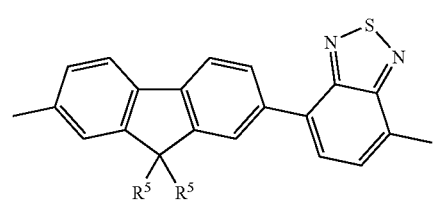
13

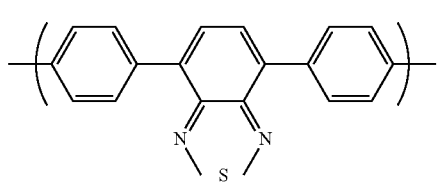
14

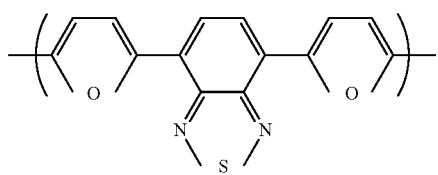
15

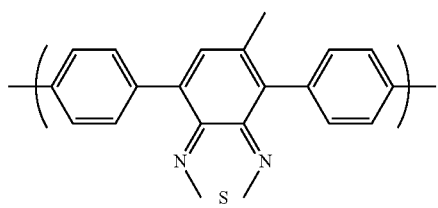
16

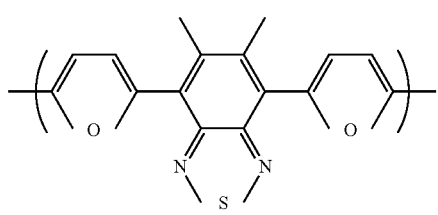
17

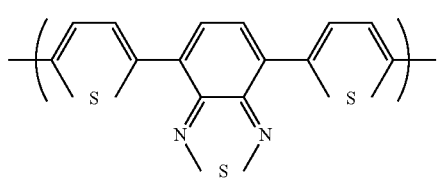
18

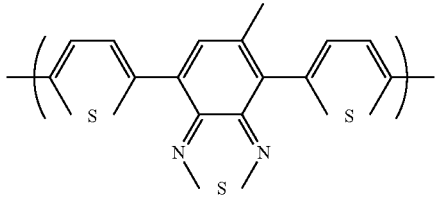
19

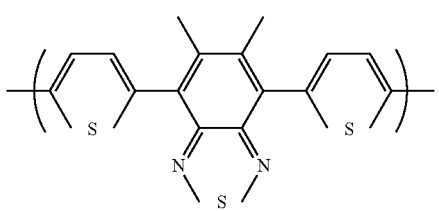
20

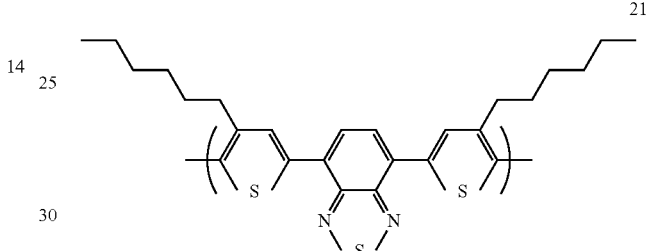
21

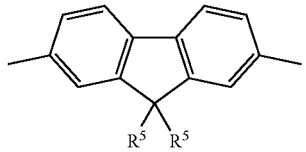
22

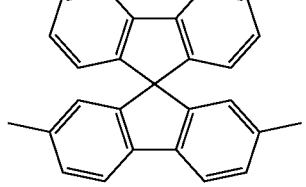
23

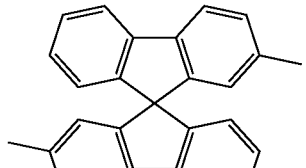
24 wherein each $R^5$ is independently selected from hydrogen, optionally substituted alkyl, alkoxy, aryl, heteroaryl, arylalkyl, alkylaryl, aryloxy, arylalkyloxy or alkylaryloxy.

Preferably, optionally substituted alkyl is $C_1$-$C_{20}$-alkyl, which can be each straight-chain, branched or cyclic, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred methyl, ethyl, n-propyl, i-propyl, n-butyl, i-butyl, s-butyl, t-butyl, n-pentyl, s-pentyl, cyclopentyl, n-hexyl, cyclohexyl, n-octyl or cyclooctyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, arylalkyl is $C_7$-$C_{20}$-arylalkyl, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred o-tolyl, m-tolyl, p-tolyl, 2,6-dimethylphenyl, 2,6-diethylphenyl, 2,6-di-i-propylphenyl, 2,6-di-t-butylphenyl, o-t-butylphenyl, m-t-butylphenyl or p-t-butylphenyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryl is $C_7$-$C_{20}$-alkylaryl, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^3$—, in particular preferred benzyl, ethylphenyl, propylphenyl, diphenylmethyl, triphenylmethyl or naphthalinylmethyl, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryl is $C_6$-$C_{20}$-aryl, in particular preferred phenyl, biphenyl, naphthyl, anthracenyl, triphenylenyl, [1,1';3',1"]terphenyl-2'-yl, binaphthyl or phenanthreny.l Preferably, heteroaryl is $C_5$-$C_{20}$-heteroaryl, in particular preferred 2-pyridyl, 3-pyridyl, 4-pyridyl, chinolinyl, isochinolinyl, acridinyl, benzochinolinyl or benzoisochinolinyl.

Preferably, alkoxy is $C_1$-$C_{20}$-alkoxy, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, in particular preferred methoxy, ethoxy, n-propoxy, i-propoxy, n-butoxy, i-butoxy, s-butoxy or t-butoxy, and $R^{10}$, $R^{11}$, $R^{12}$, $R^{13}$ are identical or different and are hydrogen or an aliphatic or aromatic hydrocarbon radical having 1 to 20 carbon atoms.

Preferably, aryloxy is $C_6$-$C_{20}$-Aryloxy, in particular preferred phenoxy, naphthoxy, biphenyloxy, anthracenyloxy or phenanthrenyloxy.

Preferably, arylalkyloxy is $C_7$-$C_{20}$-arylalkyloxy where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

Preferably, alkylaryloxy is $C_7$-$C_{20}$-alkylaryloxy, where one or more non-adjacent CH2 groups may be replaced by oxygen, sulphur, —CO—, —COO—, —O—CO—, $NR^{10}$—, —$(NR^{11}R^{12})^+$-$A^-$ or —$CONR^{13}$—, and $R^{10}$, $R^{11}$, $R^{12}$, $R^{13}$ are identical or different and are hydrogen or an aliphatic or aromatic hydrocarbon radical having 1 to 20 carbon atoms.

The polymer may have hole transporting, electron transporting and/or emissive properties. The polymer may have one or more of these properties. Where the polymer has more than one of these properties, different properties may be provided by different segments of the polymer, in particular segments of the polymer backbone as described in WO 00/55927 or pendant groups as described in WO 02/26859. Alternatively, if the polymer of the invention has only one or two of the properties of hole transport, electron transport and emission, it may be blended with one or more further polymers having the remaining required property or properties.

Preferred methods for polymerisation of these monomers are Suzuki polymerisation as described in, for example, WO 00/53656 and Yamamoto polymerisation as described in, for example, T. Yamamoto,"Electrically Conducting And Thermally Stable π-Conjugated Poly(arylene) s Prepared by Organometallic Processes", Progress in Polymer Science 1993, 17, 1153-1205 or Stille coupling. For example, in the synthesis of a linear polymer by Yamamoto polymerisation, a monomer having two reactive halide groups P is used. Similarly, according to the method of Suzuki polymerisation, at least one reactive group P is a boron derivative group.

As alternatives to halogens as described above, leaving groups of formula —O—SO2Z can be used wherein Z is as defined above. Particular examples of such leaving groups are tosylate, mesylate and triflate.

Suzuki polymerisation employs a Pd(0) complex or a Pd(II) salt. Preferred Pd(0) complexes are those bearing at least one phosphine ligand such as Pd(Ph3P)4. Another preferred phosphine ligand is tris(ortho-tolyl) phosphine, i.e. Pd(o-Tol)3.

Preferred Pd (II) salts include palladium acetate, i.e. Pd(OAc)2. Suzuki polymerisation is performed in the presence of a base, for example sodium carbonate, potassium phosphate or an organic base such as tetraethylammonium carbonate.

Yamamoto polymerisation employs a Ni(0) complex, for example bis(1,5-cyclooctadienyl)nickel(0).

Suzuki polymerisation may be used to prepare regioregular, block and random copolymers. In particular, random copolymers may be prepared when one reactive group P is a halogen and the other reactive group P is a boron derivative group.

Alternatively, block or regioregular, in particular AB, copolymers may be prepared when both reactive groups of a first monomer are boron and both reactive groups of a second monomer are halide.

Polymers made in accordance with the invention may be used in any of the aforementioned optical devices. In forming these devices, the polymer may deposited from solution by any one of a range of techniques including in particular techniques such as spin-coating, inkjet printing as disclosed in EP 0880303, laser transfer as described in EP 0851714, flexographic printing, screen printing and doctor blade coating.

A PLED comprises an electroluminescent polymer between an anode and a cathode and is supported on a substrate.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

Although not essential, the presence of a layer of organic hole injection material over the anode is desirable as it assists hole injection from the anode into the layer or layers of semiconducting polymer. Examples of organic hole injection materials include PEDT/PSS as disclosed in EP 0901176 and EP 0947123, or polyaniline as disclosed in U.S. Pat. No. 5,723,873 and U.S. Pat. No. 5,798,170.

The cathode is selected in order that electrons are efficiently injected into the device and as such may comprise a single conductive material such as a layer of aluminium. Alternatively, it may comprise a plurality of metals, for example a bilayer of calcium and aluminium as disclosed in WO 98/10621, or a thin layer of dielectric material such as lithium fluoride to assist electron injection as disclosed in, for example, WO 00/48258. The device is preferably encapsulated with an encapsulant to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142.

In a practical device, at least one of the electrodes is semi-transparent in order that light may be absorbed (in the case of a photoresponsive device) or emitted (in the case of a PLED). Where the anode is transparent, it typically comprises indium tin oxide.

Examples of transparent cathodes are disclosed in, for example, GB 2348316.

The PLED may be a static image device, i.e. a device that displays only a single image. in the simplest case, the device comprises an anode, cathode and electroluminescent polymer, each of which are unpatterned. Such a device may be suitable for lighting applications or signs displaying a fixed image. Alternatively, the device may be a variable image device, i.e. a device wherein different areas of the electroluminescent layer may be independently addressed. Such a device may be a segmented, passive matrix or active matrix device.

Polymers formed by the method of the invention may also be used in switching devices. In particular, they may be used in a field effect transistor comprising an insulator having a first side and a second side; a gate electrode located on the first side of the insulator; a polymer made by the method of the invention located on the second side of the insulator; and a drain electrode and a source electrode located on the polymer. Unlike the aforementioned optoelectronic devices, it will be appreciated that a transparent electrode is not a requirement for a switching device. Such a field effect transistor may be used in an integrated circuit.

EXAMPLES 2-(N-methyl-N-methoxyamido)-4,4'-dibromobiphenyl

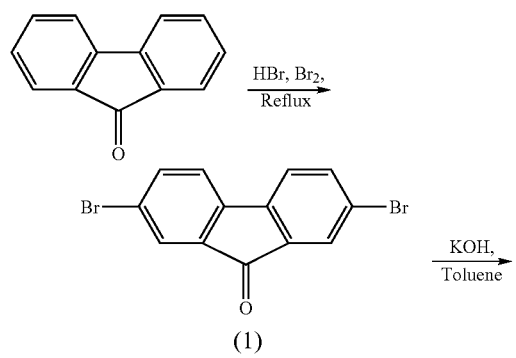

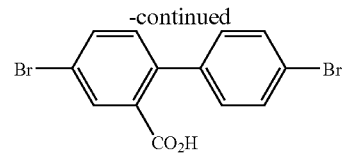

(2)

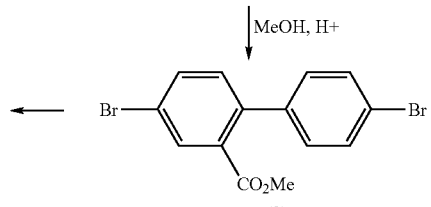

(3)

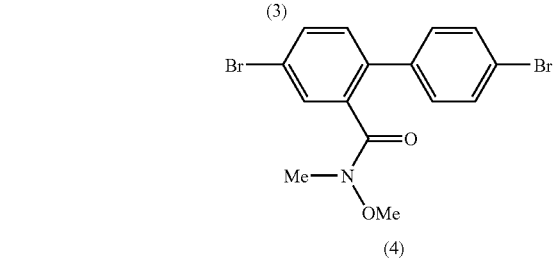

(4)

NMR uses a Varian 400 MHz system, using $CDCl_3$ (unless indicated otherwise) with a TMS standard.

(1) 2,7-Dibromofluorenone

To a 3 L round bottom flask, equipped with reflux condenser, off-gas scrubber, mechanical stirrer and nitrogen bubbler was added fluorenone (100.006 g, 0.555 mol), phosphorus pentoxide (110.148 g, 0.776 mol) and trimethylphosphite (1200 mL). Under mechanical stirring, a solution of bromine (63 mL, 1.23 mol) in trimethylphosphite (200 mL) was quickly added. This clear solution was then heated for 22 hours at 120° C. The mixture was allowed to cool to room temperature, then poured into 3 L of water. When sodium thiosulfate was added (50.045 g) the mixture turned yellow. Stirring was maintained for 1 hour, then the yellow solid was filtered. This solid was heated in methanol to remove the mono-brominated compound and gave 176.183 g (98% pure by HPLC, 94% yield).

$^1$H NMR ($CDCl_3$) 7.73 (2H, d, J2.0), 7.61 (2H, dd, J7.6, 2.0), 7.36 (2H, d, J8.0); $^{13}$C NMR ($CDCl_3$) 142.3, 137.5, 135.3, 127.9, 123.3, 121.8, 109.8.

(2) 4,4'-Dibromo-2-carboxylic acid-1,1'-biphenyl

To a 5 L 3-necked flask, equipped with reflux condenser, nitrogen bubbler and overhead mechanical stirrer, was added 2,7-dibromofluorenone (533.0 g, 1.582 mol), potassium hydroxide (finely powdered flakes, 300.0 g, 5.357 mol, 3.39 eq.) and toluene (3000 mL). The resulting mixture was heated at 120° C. for six hours then left to cool to room temperature. During this time, the appearance of the solution changed from a bright orange thin suspension into a completely white, thick suspension.

In a 10 L beaker, equipped with mechanical stirrer was added deionised water and then the cooled suspension was added over 3 minutes. The residual material in the flask was rinsed using extra toluene (2×500 mL). The resulting mixture was stirred at room temperature for 30 mins, allowing the potassium salt to dissolve. The toluene phase was removed and extracted twice with deionised water (1000 mL). The toluene phase was then discarded and the aqueous phases combined and acidified to pH 1-3 using concentrated hydrochloric acid (10M) added dropwise from a dropping funnel. During this time, the product evolved as a white suspension. The mixture was allowed to settle and the excess aqueous removed by decantation. The resulting product slurry was then filtered and the cake rinsed with fresh water (1000 mL) until the liquors were about pH 3-4. The cake was air dried and then dried in vacuo for 18 hours at 65° C. The product was afforded as an off-white solid (468 g, 83%). $^1$H NMR ((CD$_3$)$_2$CO) 8.00 (1H, d, J2.0), 7.77 (1H, dd, J8.0, 2.4), 7.57 (2H, d, J8.0), 7.34 (1H, d, J8.4), 7.29 (2H, d, J8.8); $^{13}$C NMR ((CD$_3$)$_2$CO) 167.1, 140.4, 139.8, 134.2, 133.5, 132.8, 132.7, 131.2, 130.6, 121.4, 121.1.

(3) 4,4'-Dibromo-2-methyl ester-1,1'-biphenyl

To a 5 L 3-neck round-bottom flask, equipped with reflux condenser, nitrogen bubbler and mechanical stirrer was added 4,4-dibromo-2-carboxylic (467.8 g, 1.264 mol) and methanol (3000 mL). Sulfuric acid (50 mL) was then added cautiously and the mixture then heated to 90° C. for 21 hours. The suspended solid had all dissolved after this time to form a transparent solution. The solution was allowed to cool slightly (by about 10° C.) and then solid sodium carbonate (~75 g) added portionwise, until any sign of effervescence ceased. The hot solution was stirred for 5 minutes then the stirrer stopped and the solids allowed to settle. The hot solution was then decanted into a 5 L round bottom flask equipped with mechanical stirrer (filtering was found to cause rapid crystallisation of the product) and allowed to crystallise overnight. The solid was collected by filtration and washed with cold methanol. The solid was air dried and then dried in vacuo at 45° C. The product was isolated as a white solid (354 g, 76%).

$^1$H NMR (CDCl$_3$) 7.99 (1H, d, J2.0), 7.64 (1H, dd, J8.0, 1.6), 7.51 (2H, d, J8.4), 7.19 (1H, d, J8.8), 7.13 (2H, d, J8.8), 3.67 (3H, s); $^{13}$C NMR (CDCl$_3$) 167.1, 140.3, 139.1, 134.4, 132.9, 132.1, 132.0, 131.3, 129.8, 121.9, 121.5, 52.3. GCMS: M$^+$=370, purity 99.5%+.

Literature ref: J.Am.Chem.Soc., 114, 15 (1992)

(4) Amide Intermediate: 2-(N,N-dimethylamido)-4,4'-dibromo-1,1'-biphenyl

To a 5 L 3-neck round-bottom flask, equipped with reflux condenser, nitrogen bubbler, 500 mL graduated pressure-equalised addition funnel, internal low temperature thermometer (−100 to +30° C.) and mechanical stirrer was added 4,4-dibromo-2-methyl ester-1,1'-biphenyl (716.49 g, 1.936 mol, 1.0 eq.) in anhydrous tetrahydrofuran (THF) (1500 mL). To the stirred solution was added N,N-dimethylhydroxylamine hydrochloride (288 g, 3.0 mol, 1.55 eq.) and the resulting suspension cooled to −20° C. Iso-propylmagnesium chloride (2.0M in THF) was then added over about 1 hour, ensuring the internal temperature of the mixture did not rise about −5° C. The resulting solution was then allowed to warm to ambient temperature over about 16 hours. The reaction mixture was carefully diluted with toluene (2 L) and then quenched into a 10 L beaker containing 5 L of 2M aqueous hydrochloric acid solution. The resulting mixture was stirred at ambient for 30 minutes and the toluene phase separated. The aqueous phase was extracted with toluene (2 L) and the organic phases combined and evaporated to dryness in vacuo. The resulting product was then triturated from Methanol (1500 mL). The product (white solid) was collected by filtration and washed with cold Methanol (500 mL). The product was then dried for 16 hours in vacuo at 45° C. The product was afforded as a white solid (521 g, 67%), purity 99.5%+ by GCMS.

This amide, hereinafter referred to as amide 1 was used to prepare a range of asymmetric compounds according to the following scheme, wherein S1, S2 and M are as defined in the claims.

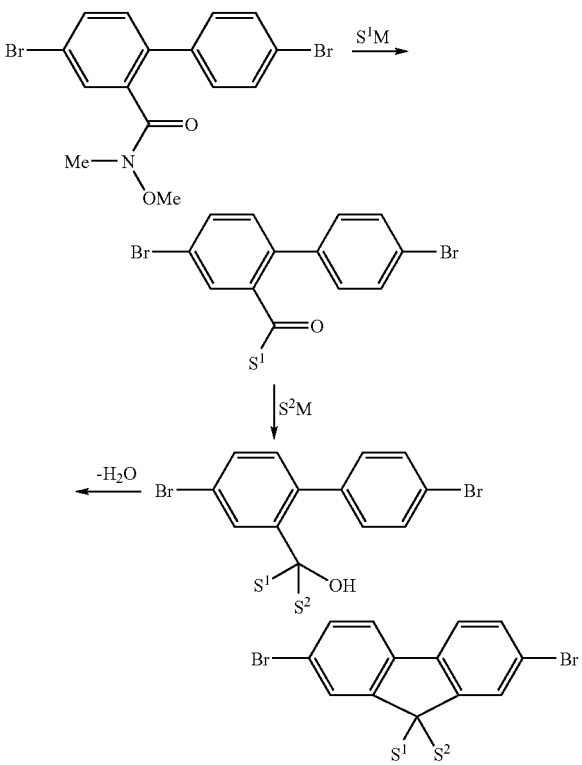

Ketone 1: 4,4'-Dibromo-1,1'-biphenyl-2-yl-4''-t-butylphenyl methanone

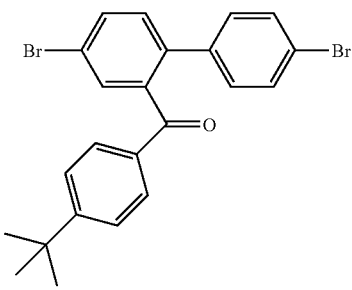

To a 3 L, 3-necked round bottom flask, equipped with mechanical stirrer, low temperature thermometer (−100 to +30° C.), nitrogen inlet and bubbler, and 500 mL graduated pressure-equalising dropping funnel, was added amide 1 (275.67 g, 0.691 mol, 1.0 eq.) and anhydrous THF (500 mL). The resulting suspension was stirred under nitrogen and cooled to −5° C. (MeOH-Cardice) and then tert-butylphenylmagnesium chloride (2M in diethyl ether, 380 mL, 0.76 mol, 1.1 eq.) was added at such a rate as to maintain the internal temperature of the vessel between −5 and 0° C. The resulting suspension was then allowed to warm to room temperature and stirred for 16 hours.

The reaction mixture was carefully diluted with toluene (1 L) poured into a 5 L beaker containing 2M aqueous hydrochloric acid solution (2 L) and the mixture-stirred by a mechanical stirrer for 30 minutes. The stirrer was stopped and the layers allowed to settle. The organic phase was removed by residual vacuum transfer and the aqueous phase extracted with a further 1 L of toluene. The organic phases were combined and concentrated to dryness in vacuo on a rotary evaporator. The resulting crude product was suspended in methanol (1250 mL) and stirred at room temperature for 16 hours (trituration). The product was then recovered by filtration using Buchner apparatus and the cake washed with fresh methanol (2×350 mL). The cake was air dried and the solid then dried at 45° C. in vacuo for 16 hours.

The product ketone was afforded as a white solid (266.95 g, 74%). The product was analysed by GC-MS and found to display m/z 472 (M+) and a single peak (estimated purity 99.8%).

Asymmetric Compound 1 Precursor: 4,4'-Dibromo-2-phenyl(4-tert-butylphenyl)hydroxymethyl-1,1'-biphenyl

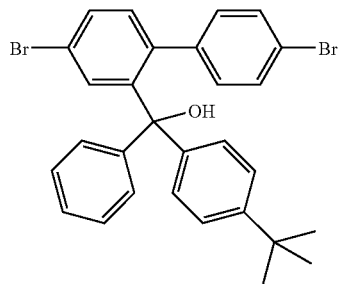

To a 250 mL round bottomed flask, equipped with low temperature thermometer (−100 to +30° C.), magnetic stirrer bar, 100 mL graduated pressure-equalised dropping addition funnel and nitrogen inlet and bubbler was added bromobenzene (7.98 g, 5.35 mL, 50.82 mmol, 1.2 eq.) and anhydrous THF (50 mL) and the resulting solution cooled to −72° C. (acetone-cardice). N-Butyllithium (2.5M in hexanes) (22.02 mL, 55.06 mmol, 1.3 eq.) was added dropwise, maintaining the internal temperature below −65° C. After complete addition, the solution was maintained at −70° C. and stirred for 1 hour. A solution of ketone 1 (20.0 g, 42.35 mmol, 1.0 eq.) in anhydrous THF (50.0 mL) was added, keeping the internal temperature below −60° C. The solution was allowed to warm to room temperature over 4 hours, then quenched into 2M aqueous hydrochloric acid solution (250 mL). The products were extracted into toluene (2×250 mL), the organic phases combined and evaporated to dryness in vacuo on a rotary evaporator. IPA was added (200 mL) and the product crystallised over 16 hours. The product was recovered by filtration and the cake washed with cold isopropyl alcohol (50 mL). The product was then air dried and dried at 45° C. in vacuo for 16 hours. A second crop was crystallised from the liquors.

The product was afforded as a white solid (18.63 g, 80%). The product was analysed by GCMS and displayed an m/z-H$_2$O peak at m/z 532. Purity estimated at 99%$_+$.

Asymmetric Compound 1: 9-phenyl-9'-(tert-butylphenyl-2,7-dibromofluorene

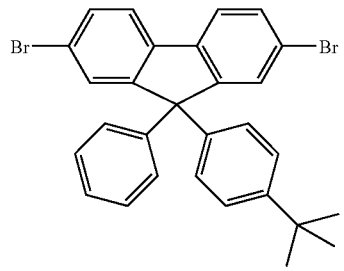

To a 250 mL round bottomed flask, equipped with magnetic stirrer bar, reflux condenser and nitrogen inlet and bubbler was added asymmetric compound 1 precursor (6.87 g, 12.5 mmol, 1.0 eq.) and glacial acetic acid (100 mL). To the stirred suspension at room temperature was added concentrated hydrochloric acid (2 mL) and the resulting suspension heated to reflux. After 5 hours at reflux, in-process check indicated the reaction to be complete (GCMS). The solution was allowed to cool to room temperature and poured into water (200 mL) with stirring for 10 minutes. This caused precipitation of the product which was recovered by filtration. The filter cake was washed with water (2×100 mL) and then displacement wash with methanol (100 mL). The crude product was recrystallised from a mixture of acetonitrile and toluene to afford asymmetric compound 1 as a white solid (3.2 g, 48%).

HPLC indicated 99.2% purity. GCMS indicated the correct product (m/z 532).

Asymmetric Compound 2 Precursor: 4,4'-Dibromo-2-biphenyl(tert-butylphenyl)hydroxymethyl-1,1'-biphenyl)

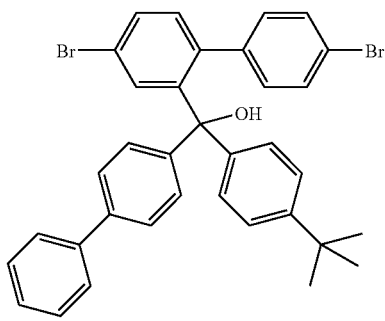

To a 250 mL round bottomed flask, equipped with low temperature thermometer (−100 to +30° C.), magnetic stirrer bar, 100 mL graduated pressure-equalised dropping addition funnel and nitrogen inlet and bubbler was added 4-bromobiphenyl (15.99 g, 68.6 mmol, 1.2 eq.) and anhydrous THF (100 mL) and the resulting solution cooled to −72° C. (acetone-Cardice). N-Butyllithium (2.5M in hexanes) (29.73 mL, 74.30 mmol, 1.3 eq.) was added dropwise, maintaining the internal temperature below −65° C. After complete addition, the solution was maintained at −70° C. and stirred for 1 hour. A solution of ketone 1 (27.0 g, 57.2 mmol, 1.0 eq.) in anhydrous THF (75 mL) was added, keeping the internal temperature <−60° C. The solution was allowed to warm to room temperature (RT) over 4 hours, and then quenched into 2M aqueous hydrochloric acid solution (500 mL). The products were extracted into toluene (2×350 mL), and the organic phases combined and washed to neutrality with water (3×500 mL). The organic phases were combined and evaporated to dryness in vacuo on a rotary evaporator. Acetonitrile was added (200 mL) and the product crystallised over 16 hours. The product was recovered by filtration and the cake washed with cold acetonitrile (50 mL). The product was air dried and then dried at 45° C. in vacuo for 16 hours. A second crop was crystallised from the liquors.

The product was afforded as a white solid (26.5 g, 74%). The product was analysed by GCMS and displayed an m/z-H$_2$O peak at m/z 611. Purity estimated at 95%+.

Asymmetric Compound 2: 9-biphenyl-9-(4-tert-butylphenyl)-2,7-dibromofluorene

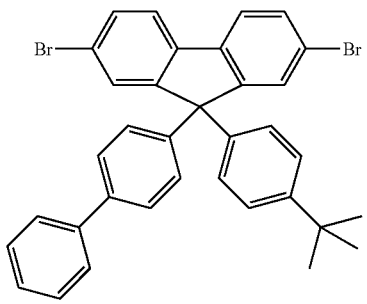

To a 250 mL round bottomed flask, equipped with magnetic stirrer bar, reflux condenser and nitrogen inlet and bubbler was added the asymmetric compound 2 precursor (26 g, 41.5 mmol, 1.0 eq.) and glacial acetic acid (500 mL). To the stirred suspension at room temperature was added concentrated hydrochloric acid (1 mL) and the resulting suspension heated to reflux. After 2 hours at reflux, in-process check indicated the reaction to be complete (GCMS). The solution was allowed to cool to room temperature and poured into water (2 L) with stirring for 10 minutes. This caused precipitation of the product which was recovered by filtration. The filter cake was washed with water (3×1 L) and then displacement wash with methanol (500 mL). The crude product was recrystallised from a mixture of acetonitrile and toluene to afford the product as a white solid (13.7 g, 54%). HPLC indicated 99.42% purity. GCMS indicated the correct product (m/z 609).

Asymmetric Compound 3 Precursor: 4,4'-Dibromo-2-(4'-tert-butyl-1,1'-biphenyl)-(tert-butylphenyl)hydroxymethyl-1,1'-biphenyl

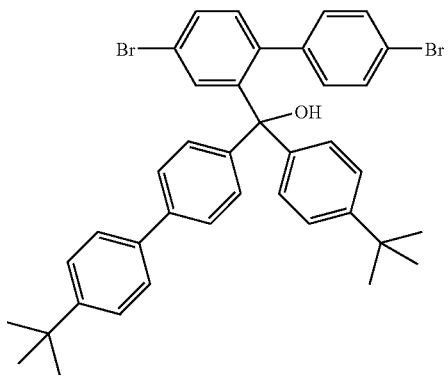

To a 500 mL round bottomed flask, equipped with low temperature thermometer (−100 to +30° C.), mechanical stirrer, 100 mL graduated pressure-equalised dropping addition funnel and nitrogen inlet and bubbler was added 4-tert-butyl-4'-bromo-1,1'-biphenyl (11.36 g, 39.28 mmol, 1.2 eq.) and anhydrous THF (100 mL) and the resulting solution cooled to −72° C. (acetone-Cardice). N-Butyllithium (2.5M in hexanes) (21.28 mL, 42.55 mmol, 1.3 eq.) was added dropwise, maintaining the internal temperature below −65° C. After complete addition, the solution was maintained at −70° C. and stirred for 1 hour. A solution of ketone 1 (15.45 g, 32.73 mmol, 1.0 eq.) in anhydrous THF (125.0 mL) was added, keeping the internal temperature <−60° C. The solution was allowed to warm to RT over 4 hours, then quenched into 2M aqueous hydrochloric acid solution (500 mL). The products were extracted into toluene (2×500 mL), the organic phases combined and washed with water to neutrality (3×500 mL). The toluene phase was evaporated to dryness in vacuo on a rotary evaporator. Acetonitrile was added (200 mL) and the product crystallised over 16 hours. The product was recovered by filtration and the cake washed with cold IPA (50 mL). The product was then air dried and dried at 45° C. in vacuo for 16 hours. A second crop was crystallised from the liquors.

The product was afforded as a white solid (14 g, 52%). Purity estimated at 99%+.

Asymmetric Compound 3: 9-(4'-tert-butyl-1,1'-biphenyl)-9-(4-tert-butylphenyl)-2,7-dibromofluorene

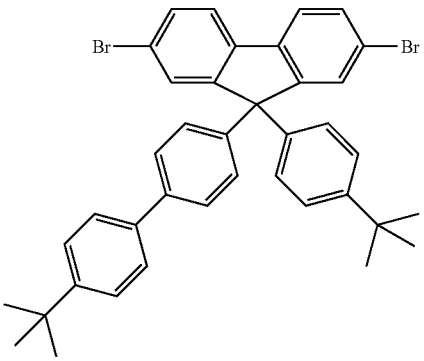

To a 1 L round bottomed flask, equipped with magnetic stirrer bar, reflux condenser and nitrogen inlet and bubbler was added asymmetric compound 3 precursor (14 g, 20.5 mmol, 1.0 eq.) and glacial acetic acid (500 mL). To the stirred suspension at room temperature was added concentrated hydrochloric acid (2 mL) and the resulting suspension heated to reflux. After 3 hours at reflux, in-process check indicated the reaction to be complete (GCMS). The solution was allowed to cool to room temperature and poured into water (2 L) with stirring for 10 minutes. This caused precipitation of the product which was recovered by filtration. The filter cake was washed with water (2×1 L). The crude product was recrystallised from a mixture of acetonitrile and toluene to afford asymmetric compound 3 as a white solid (10.63 g, 78%).

HPLC indicated 99.6% purity. GCMS indicated the correct product (m/z 664).

Asymmetric Compound 4 Precursor: 4,4'-dibromo-2-(4-tert-butylphenyl)-2-thienyl-hydroxymethyl-1,1'-biphenyl

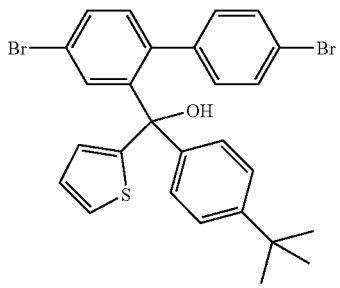

To a 500 mL round bottomed flask, equipped with low temperature thermometer (−100 to +30° C.), mechanical stirrer, 100 mL graduated pressure-equalised dropping addition funnel and nitrogen inlet and bubbler was added 2-bromothiophene (6.21 g, 38.11 mmol, 1.2 eq.) and anhydrous THF (100 mL) and the resulting solution cooled to −72° C. (acetone-cardice). N-Butyllithium (2.5M in hexanes) (20.64 mL, 41.29 mmol, 1.3 eq.) was added dropwise, maintaining the internal temperature below −65° C. After complete addition, the solution was maintained at −70° C. and stirred for 1 hour. A solution of ketone 1 (15.0 g, 31.76 mmol, 1.0 eq.) in anhydrous THF (125.0 mL) was added, keeping the internal temperature <−60° C. The solution was allowed to warm to RT over 4 hours, then quenched into 2M aqueous hydrochloric acid solution (500 mL). The products were extracted into toluene (2×300 mL), the organic phases combined and washed with water to neutrality (3×500 mL). The toluene phase was evaporated to dryness in vacuo on a rotary evaporator. The product was purified by column chromatography using a mixture of dichloromethane and hexanes (1:1).

The product was afforded as a red solid (15 g, 72%). The product was analysed by GCMS and displayed an m/z-H$_2$O peak at m/z 538. Purity estimated at 96.8%+.

Asymmetric Compound 4: 9-(4-tert-butylphenyl)-9-thien-2-yl-2,7-dibromofluorene

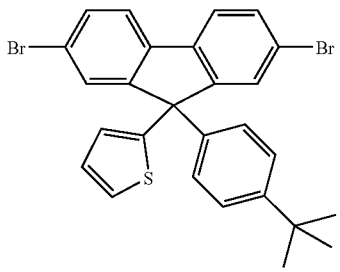

To a 500 mL round bottomed flask, equipped with magnetic stirrer bar, reflux condenser and nitrogen inlet and bubbler was added the asymmetric compound 4 precursor (15.1 g, 27.15 mmol, 1.0 eq.) and glacial acetic acid (500 mL). To the stirred suspension at room temperature was added concentrated hydrochloric acid (2 mL) and the resulting suspension heated to reflux. After 4 hours at reflux, in-process check indicated the reaction to be complete (GCMS). The solution was allowed to cool to room temperature and poured into water (1000 mL) with stirring for 10 minutes. This caused precipitation of the product which was recovered by filtration. The filter cake was washed with water (2×1 L). The crude product was triturated from hexanes to afford asymmetric compound 4 as a dark solid (14 g, 90%).

HPLC indicated >80% purity.

Ketone 2: [4,4-dibromo-1,1'-biphenyl]-2-yl-n-octyl ketone

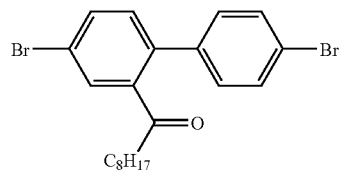

To a 500 mL round bottomed 3-necked flask, equipped with mechanical stirrer, reflux condenser, 100 mL pressure-equalised dropping addition funnel, nitrogen inlet and bubbler and low temperature thermometer (−100 to +30° C.) was added amide 1 (30.0 g, 75.2 mmol, 1.0 eq.) and anhydrous THF (200 mL). The resulting solution was stirred under nitrogen and cooled to −20° C. (MeOH-cardice). A solution of n-octylmagnesium bromide (2.0M in THF, 48.7 mL, 97.7 mmol, 1.3 eq.) was added dropwise, maintaining the internal solution temperature below −10° C. After complete addition, the solution was allowed to warm to room temperature overnight. The reaction mixture was poured into 2M aqueous hydrochloric acid solution (500 mL) and the products extracted into toluene (2×300 mL). The toluene extracts were washed with water (3×500 mL). The toluene phase was then concentrated to dryness in vacuo using a rotary evaporator.

The crude product was purified using column chromatography using 100% hexanes to 4:1 dichloromethane:hexanes as eluant. Product was isolated as an oil (22.91 g, 67.4%). GCMS indicated m/z 452, purity almost 100%.

Asymmetric Compound 5 Precursor: 4,4'-Dibromo-2-n-octyl-2-phenylhydroxymethyl-1,1'-biphenyl

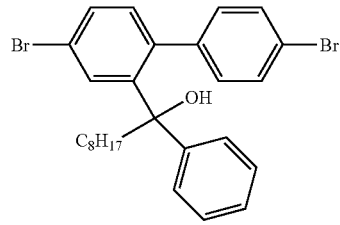

To a 500 mL round bottomed flask, equipped with low temperature thermometer (−100 to +30° C.), mechanical stirrer, 100 mL graduated pressure-equalised dropping addition funnel and nitrogen inlet and bubbler was added bromobenzene (9.55 g, 60.79 mmol, 1.2 eq.) and anhydrous THF (150 mL) and the resulting solution cooled to −72° C. (acetone-cardice). N-Butyllithium (2.5M in hexanes) (26.34 mL, 65.86 mmol, 1.3 eq.) was added dropwise, maintaining the internal temperature below −65° C. After complete addition, the solution was maintained at −70° C. and stirred for 1 hour. A solution of ketone 2 (22.91 g, 50.66 mmol, 1.0 eq.) in anhydrous THF (125.0 mL) was added, keeping the internal temperature <−60° C. The solution was allowed to warm to RT over 4 hours, then quenched into 2M aqueous hydrochloric acid solution (500 mL). The products were extracted into toluene (2×300 mL), the organic phases combined and washed with water to neutrality (3×500 mL). The toluene phase was evaporated to dryness in vacuo on a rotary evaporator. The product was purified by column chromatography using a mixture of dichloromethane and hexanes (1:4).

The product was afforded as a colourless oil (12.1 g, 45%). The product was analysed by GCMS and displayed an m/z-H$_{ny}$O peak at m/z 512. Purity estimated at 87%+.

Asymmetric Compound 5:
9-n-octyl-9-phenyl-2,7-dibromofluorene

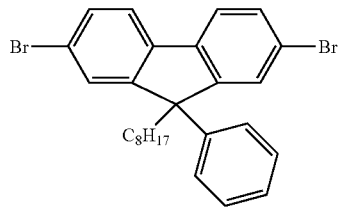

To a 500 mL round bottomed flask, equipped with magnetic stirrer bar, reflux condenser and nitrogen inlet and bubbler was added the asymmetric compound 5 precursor (12.1 g, 22.83 mmol, 1.0 eq.) and glacial acetic acid (500 mL). To the stirred suspension at room temperature was added concentrated hydrochloric acid (2 mL) and the resulting suspension heated to reflux. After 4 hours at reflux, in-process check by GCMS indicated the reaction to be complete. The solution was allowed to cool to room temperature and poured into water (1 L) with stirring for 10 minutes. This caused precipitation of the product which was recovered by filtration. The filter cake was washed with water (2×1 L). The crude product was triturated from hexanes to afford asymmetric compound 5 as an oil (10 g, 83%).

GCMS indicated 97.06% purity.

Ketone 3: [4,4'-Dibromo-1,1'-biphenyl]-2-yl phenyl ketone

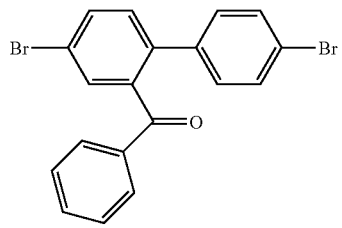

To a 2 L, 3-necked round bottom flask, equipped with mechanical stirrer, low temperature thermometer (−100 to +30° C.), nitrogen inlet and bubbler, and 500 mL graduated pressure-equalising dropping funnel, was added amide 1 (150 g, 0.376 mol, 1.0 eq.) and anhydrous THF (500 mL). The resulting solution was stirred under nitrogen and cooled to −5° C. (MeOH-cardice) and then phenylmagnesium bromide (3M in THF, 140 mL, 0.414 mol, 1.1 eq.) was added at such a rate as to maintain the internal temperature of the vessel between −5 and 0° C. The resulting suspension was then allowed to warm to room temperature and stirred for 16 hours.

The reaction mixture was carefully diluted with toluene (1 L) poured into a 5 L beaker containing 2M aqueous hydrochloric acid solution (2 L) and the mixture stirred by a mechanical stirrer for 30 minutes. The stirrer was stopped and the layers allowed to settle. The organic phase was removed by residual vacuum transfer and the aqueous phase extracted with a further 1 L of toluene. The organic phases were combined and concentrated to dryness in vacuo on a rotary evaporator. The resulting crude product was suspended in methanol (750 mL) and stirred at room temperature for 16 hours (trituration). The product was then recovered by filtration using Buchner apparatus and the cake washed with fresh methanol (2×250 mL). The cake was air dried and the solid then dried at 45° C. in vacuo for 16 hours.

The product ketone was afforded as a white solid (147.84 g, 94%). The product was analysed by GC-MS and found to display m/z 416 (M+) and a single peak (estimated purity 99.8%).

Asymmetric Compound 6 Precursor: 4,4'-dibromo-2-phenyl(4-decyloxyphenyl)hydroxymethyl-1,1'-biphenyl)

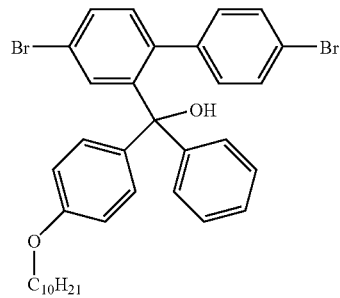

To a 250 mL round bottomed flask, equipped with low temperature thermometer (−100 to +30° C.), magnetic stirrer bar, 100 mL graduated pressure-equalised dropping addition funnel and nitrogen inlet and bubbler was added 4-decyloxybenzene (16.5 g, 53.0 mmol, 1.1 q.) and anhydrous THF (100 mL) and the resulting solution cooled to −72° C. (acetone-cardice). N-Butyllithium (2.5M in hexanes) (23.0 mL, 58.0 mmol, 1.2 eq.) was added dropwise, maintaining the internal temperature below −65° C. After complete addition, the solution was maintained at −70° C. and stirred for 1 hour. A solution of ketone 3 (20.0 g, 48.0 mmol, 1.0 eq.) in anhydrous THF (50.0 mL) was added, keeping the internal temperature <−60° C. The solution was allowed to warm to RT over 4 hours, then quenched into 2M aqueous hydrochloric acid solution (250 mL). The products were extracted into toluene (2×250 mL), the organic phases combined and evaporated to dryness in vacuo on a rotary evaporator. Isopropyl alcohol was added (200 mL) and the product crystallised over 16 hours. The product was recovered by filtration and the cake washed with cold isopropyl alcohol (50 mL). The product was then air dried and dried at 45° C. in vacuo for 16 hours.

The product was afforded as a white solid (18.6 g, 90%). The product as analysed by GCMS showed a mixture of products.

Asymmetric Compound 6 Precursor:
2,7-dibromo-9-phenyl-9-(4-decyloxyphenyl)fluorene

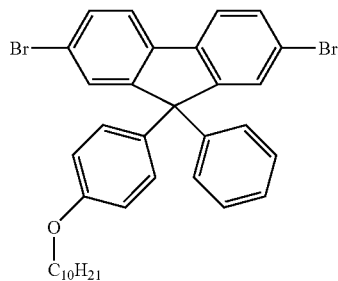

Asymmetric compound 6 was prepared by dehydration of asymmetric compound 5 according to the method described above for the preparation of asymmetric compound 1.

Pinacol diester of Asymmetric Compound 1
(Method 1): 9-phenyl-9-tert-butylphenylfluorene-2,
7-pinacolatoboron ester

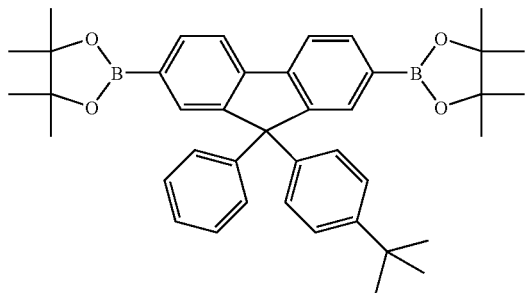

To a 3-necked round bottomed 2 L flask, equipped with mechanical stirrer, reflux condenser, nitrogen inlet and bubbler, low temperature thermometer (−100 to +30° C.) and pressure-equalised, 250 mL graduated dropping addition funnel (inerted with nitrogen before use) was added asymmetric compound 1 (54.97 g, 0.103 mol, 1.0 eq.) and anhydrous THF (550 mL). The resulting solution was cooled to −78° C. (acetone-cardice) and n-butyllithium (2.5M in hexanes) (90.64 mL, 0.227 mol, 2.2 eq.) was added dropwise so as to maintain the internal temperature below −65° C. After complete addition, the solution was stirred at −78 warming up to 8° C. for a further 1 hour, before the addition of triisopropylborate (58.12 g, 71 mL, 0.309 mol, 3.0 eq.) dissolved in anhydrous THF (160 mL), again maintaining the internal temperature below −65° C. The resulting solution was then allowed to warm slowly to room temperature.

The solution was cooled to 0° C. (ice-water) and HCl in ether solution (2M) (134 mL, 0.27 mol, 2.6 eq.) was added and the solution allowed to warm to room temperature before filtering through a No. 3 porosity sinter funnel (to remove precipitated inorganic salts). The solvent was removed in vacuo and the residue re-dissolved in toluene (250 mL). The solution was cooled and filtered (paper) into a 1 L flask. Pinacol (58.12 g, 0.27 mol, 3.0 eq.) was added, followed by para-toluenesulfonic acid (1 g) and the reaction heated under Dean-Stark conditions for 4 hours. The solution was allowed to cool and 2 g of potassium carbonate added. The mixture was stirred for 30 minutes at RT, filtered and the solution concentrated to dryness in vacuo. The solid was recrystallised from a toluene/acetonitrile mixture to afford the product, which was recovered by filtration.

The product was dried at 45° C. for 16 hours. The title compound was afforded as a white solid (43 g, 66%). HPLC indicated a purity (npa) of 93%.

Pinacol diester of Asymmetric Compound 1
(Method 2): 9-phenyl-9-tert-butylphenylfluorene-2,
7-pinacolatoboron ester

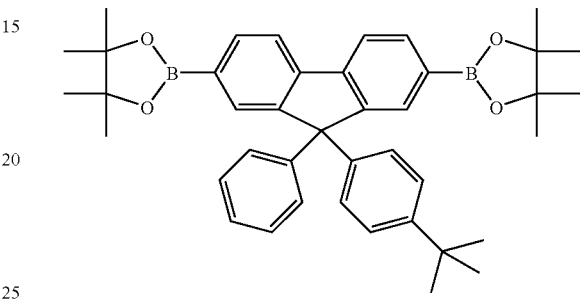

To a 500 mL 3 neck round bottomed flask, equipped with reflux condenser, mechanical stirrer and septum cap (cooled under nitrogen before use) was added asymmetric compound 1 (33 g, 62 mmol, 1.0 eq.), anhydrous toluene (400 mL), $PdCl_2[(o\text{-}tol)_3P]_2$ (2.44 g, 3.1 mmol, 5 mol %) and ortho-tolylphosphine (1.89 g, 10 mol %). The solution was degassed by sparging with nitrogen for 1 hour, then triethylamine (37.64 g, 0.186 mmol, 6.0 eq.) added, followed by degassing for 15 minutes. Pinacolborane (23.80 g, 0.186 mol, 3.0 eq.) was then added and the solution heated to reflux for 4 hours. The reaction mixture was allowed to cool to room temperature and then filtered through a short pad of silica gel, eluting with toluene (500 mL). The toluene solution was concentrated to dryness in vacuo. The crude solid was then purified by recrystallisation from a toluene/acetonitrile mixture to afford the product, which was recovered by filtration.

The product was dried at 45° C. for 16 hours. The title compound was afforded as a white solid (15 g, 39%). HPLC indicated a purity (npa) of 99%. GC-MS indicated the correct mass (m/z 626).

COMPARATIVE EXAMPLE

Synthesis of ketone 1 was attempted in accordance with the method described above, except that ester 1, shown below, was used in place of amide 1:

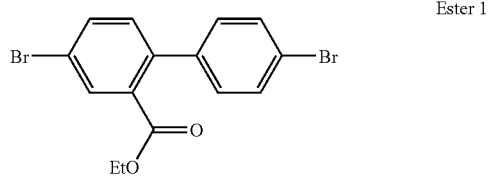

Ester 1

The product mixture was found to comprise starting material, ketone 1 and the alcohol resulting from over-reaction of ketone 1 with the Grignard reagent. Difficulty was encountered in attempting to separate these products.

Although the present invention has been described in terms of specific exemplary embodiments, it will be appreciated that various modifications, alterations and/or combinations of features disclosed herein will be apparent to those skilled in the art without departing from the spirit and scope of the invention as set forth in the following claims.

The invention claimed is:

1. A method of forming a compound of formula (IV):

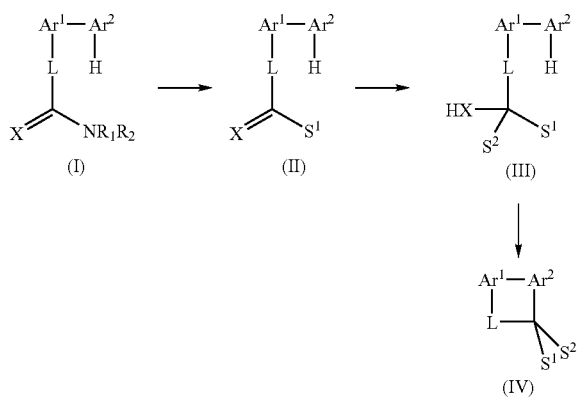

said method comprising the steps of:
a) reacting a compound of formula (I) with a compound of formula $S^1$-M to give a compound of formula (II);
b) reacting the compound of formula (II) with a compound of formula $S^2$-M to give a compound of formula (III); and
c) eliminating $H_2X$ from the compound of formula (III) to give a compound of formula (IV),
wherein
$Ar^1$ and $Ar^2$ are independently selected from optionally substituted aryl or heteroaryl groups;
X is O, S, NH or NR;
L is a bond or a linking group which contains 1, 2 or 3 atoms;
R and $R_1$ are independently selected from the group consisting of optionally substituted alkyl, aryl, alkylaryl, arylalkyl and heteroaryl groups;
$R_2$ is selected from the group consisting of alkoxy, aryloxy, arylalkyloxy, alkylaryloxy, alkylthio, arylthio, alkylarylthio and arylalkylthio;
H is bound to a carbon atom C' of $Ar^2$;
C' and the carbon atom of C=X are separated by 3-5 atoms;
$S^1$ and $S^2$ are each selected from optionally substituted alkyl, aryl or heteroaryl groups, M comprises a metal; and
M is linked to $S^1$ and $S^2$ by a carbon-metal bond.

2. A method according to claim 1 wherein alkyl is $C_1$-$C_{20}$-alkyl, arylalkyl is $C_7$-$C_{20}$-arylalkyl, alkylaryl is $C_7$-$C_{20}$-alkylaryl, aryl is $C_6$-$C_{20}$-aryl, heteroaryl is $C_5$-$C_{20}$-heteroaryl, alkoxy is $C_1$-$C_{20}$-alkoxy, aryloxy is $C_6$-$C_{20}$-Aryloxy, arylalkyloxy is $C_7$-$C_{20}$-arylalkyloxy, alkylaryloxy is $C_7$-$C_{20}$-alkylaryloxy, alkylthio is $C_1$-$C_{20}$-alkylthio, arylthio is $C_6$-$C_{20}$-arylthio, alkylarylthio is $C_7$-$C_{20}$-alkylarylthio, arylalkylthio is $C_7$-$C_{20}$-arylalkylthio.

3. A method according to claim 1 wherein $Ar^1$ and $Ar^2$ are phenyl or substituted phenyl.

4. A method according to claim 1, wherein X is O or S.

5. A method according to claim 1, wherein L is a bond.

6. A method according to claim 1, wherein R is C1-10 alkyl.

7. A method according to claim 1, wherein $R^1$ is C1-10 alkyl.

8. A method according to claim 1, wherein $R^2$ is C1-10 alkoxy.

9. A method according to claim 1, wherein M is lithium, zinc or Mg-Hal wherein Hal is a halide.

10. A method according to claim 1, wherein $S^1$ and $S^2$ are independently selected from optionally substituted aryl or alkyl.

11. A method according to claim 1, wherein $S^1$ and $S^2$ are independently selected from optionally substituted aryl or alkyl and $S^1$ and $S^2$ are different from each other.

12. A method according to claim 1, wherein $Ar^1$ and $Ar^2$ of the compound of formula (I) are each substituted with a polymerisable group P.

13. A method according to claim 1, comprising the further step of providing each of $Ar^1$ and $Ar^2$ of the compound of formula (II), (III) or (IV) with a polymerisable group P.

14. A method according to claim 12, wherein each polymerisable group P is independently a halide or a boron derivative group selected from a boronic acid group, a boronic ester group and a borane group; or a moiety of formula —O—$SO_2$-Z wherein Z is selected from the group consisting of optionally substituted alkyl and aryl.

15. A method according to claim 12 wherein each polymerisable group P is independently a leaving group capable of participating in a polycondensation reaction.

16. A method according to claim 1 wherein
$Ar^1$ and $Ar^2$ are phenyl or substituted phenyl,
X is O or S,
L is a bond,
R is C1-10 alkyl,
$R^1$ is C1-10 alkyl,
$R^2$ is C1-10 alkoxy,
M is lithium, zinc or Mg-Hal wherein Hal is a halide,
$S^1$ and $S^2$ are independently selected from optionally substituted aryl or alkyl and $S^1$ and $S^2$ are are different from each other.

* * * * *